US006707056B2

(12) United States Patent
Fanton et al.

(10) Patent No.: US 6,707,056 B2
(45) Date of Patent: Mar. 16, 2004

(54) STAGE ROTATION SYSTEM TO IMPROVE EDGE MEASUREMENTS

(75) Inventors: Jeffrey T. Fanton, Los Altos, CA (US); Craig Uhrich, Redwood City, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 10/132,959

(22) Filed: Apr. 26, 2002

(65) Prior Publication Data

US 2002/0191740 A1 Dec. 19, 2002

Related U.S. Application Data

(60) Provisional application No. 60/298,711, filed on Jun. 15, 2001.

(51) Int. Cl.[7] .............................................. G01N 21/00
(52) U.S. Cl. .................. 250/559.44; 356/237.2
(58) Field of Search ....................... 378/70; 356/237.5, 356/237.2, 237.3, 237.4; 250/559.4, 559.41, 559.42, 559.44, 559.04

(56) References Cited

U.S. PATENT DOCUMENTS 5,619,548 A    4/1997  Koppel ........................ 378/70
5,825,482 A  * 10/1998  Nikoonahad et al. .... 356/237.2
6,160,615 A  * 12/2000  Matsui et al. ............ 356/237.4

FOREIGN PATENT DOCUMENTS

JP        406003258 A  *  1/1994
WO        WO 01/71325 A2    9/2001   .......... G01N/23/00

* cited by examiner

*Primary Examiner*—David V. Bruce
*Assistant Examiner*—Hoon Song
(74) *Attorney, Agent, or Firm*—Stallman & Pollock LLP

(57) ABSTRACT

A method for operating an optical measurement system is disclosed which permits measurements to be made more uniformly in regions close the edge of a wafer. The optical measurement system includes a probe beam which is focused to an elliptically shaped spot on the surface of the wafer. Improved measurements near the wafer's edge are obtained by rotating the wafer with respect to the measurement spot to insure that the short axis of the ellipse is perpendicular to the wafer edge.

2 Claims, 5 Drawing Sheets

STAGE ROTATION SYSTEM TO IMPROVE EDGE MEASUREMENTS

The present application claims the benefit of U.S. Provisional Application Serial No. 60/298,711 filed Jun. 15, 2001, STAGE ROTATION SYSTEM TO IMPROVE EDGE MEASUREMENTS, which is incorporated herein by reference.

FIELD OF INVENTION

The present invention relates to a method of making metrology measurements of a semiconductor wafer and, in particular, includes an approach for improving measurements near the edge of the wafer.

BACKGROUND OF INVENTION

Semiconductor manufacturers are interested in taking measurements at selected points on a wafer from the center out to the edges thereof. In order to obtain accurate measurement, the focal spot of the probe beam must not extend beyond the wafer edge. As can be appreciated, any portion of the beam which extends beyond the wafer's edge will not be reflected resulting in an unexpected reduction in measured intensity which leads to errors in the analysis. In addition, edge effects can cause scattering, also reducing the accuracy of the measurement.

Because of this problem, the metrology device must be configured to limit how close the center of the focal spot can be moved to the edge during a measurement. This restriction is not typically a problem if the probe beam spot is relatively small and circular. However, when the probe beam is large and has an elliptical shape, problems arise. This problem is present with current X-ray reflection measurements and ellipsometry systems, where a focused X-ray beam is directed onto a wafer at a non-normal angle of incidence. For example, U.S. Pat. No. 5,619,548 and PCT WO 01/71325, both incorporated herein by reference describe methods and apparatus for X-ray reflectometry with a focused X-ray beam directed onto a wafer with an angle of incidence in a range between 87.8 and 89.9 degrees from normal. In another example, U.S. Pat. No. 5,973,787, also incorporated herein by reference, describes an ellipsometry system with an angle of incidence of an optical beam in the range between 30 and 70 degrees from normal.

As an example, FIG. 1 illustrates a probe beam 2 directed onto a wafer 1 at a high angle of incidence Φ as measured from the normal 12. Although the probe beam itself has a generally circular cross section, the spot 7 on the wafer surface is elliptical, having a short axis W substantially corresponding to the beam diameter and a long axis L which is dependent upon, among other factors, the angle of incidence of the beam on the sample. In particular, for a circular beam, the long axis of the elliptical beam spot is defined by $$L = d/\cos \Phi \quad [1]$$

where d is the beam diameter and Φ is the angle of incidence of the beam. As can be appreciated from equation (1), increasing the angle of incidence of the beam increase the long axis of the ellipse. For a high angle of incidence, such as used in an X-Ray reflectometer, the long axis of the ellipse can be more than five times longer than the short axis. This elliptical beam spot has caused problems when attempting to take measurements close to the edge of a wafer due to the scattering and edge effects mentioned above.

This problem will be discussed with reference to FIG. 2. More specifically, in many existing systems, the wafer rests on a movable stage. The stage is used to vary the position of the wafer with respect to the beam spot. For ease of explanation, FIG. 2 shows an X–Y coordinate system with the center of the wafer being at $O_x$, $O_y$. If it is desired to measure at a site near the top center of wafer ($O_x$, $N_y$), the stage is moved so the beam spot is located at position "A". As can be seen, the center of the beam spot can be moved quite close to the wafer edge without the edges of the beam extending beyond the wafer edge.

In contrast, if it desired to measure at position ($N_x$, $O_y$), which is a similar distance from the wafer's edge as position A, the beam spot would extend at over the edge of the wafer. Accordingly, the center of the beam spot must be moved to position B, which is farther from the edge than position A. Accessing measurement areas on a wafer using only X,Y linear motions to position an elliptical beam spot means that the area actually accessible for measurement is elliptical in configuration as indicated by ellipse 8 of FIG. 2. (It should be understood that the illustrated dimensions are not drawn to scale, particularly the beam spot which has been greatly enlarged.)

SUMMARY OF THE INVENTION

The subject method is intended to allow more uniformity at all measurement sites near the edge of the wafer around the wafer circumference. To achieve this goal, a theta (θ) or rotational stage is used to rotate the wafer so that short axis W of the ellipse is oriented perpendicular to the wafer edge when measurements at sites near the edge are desired.

DETAILED DESCRIPTION OF THE INVENTION

Figure 3:
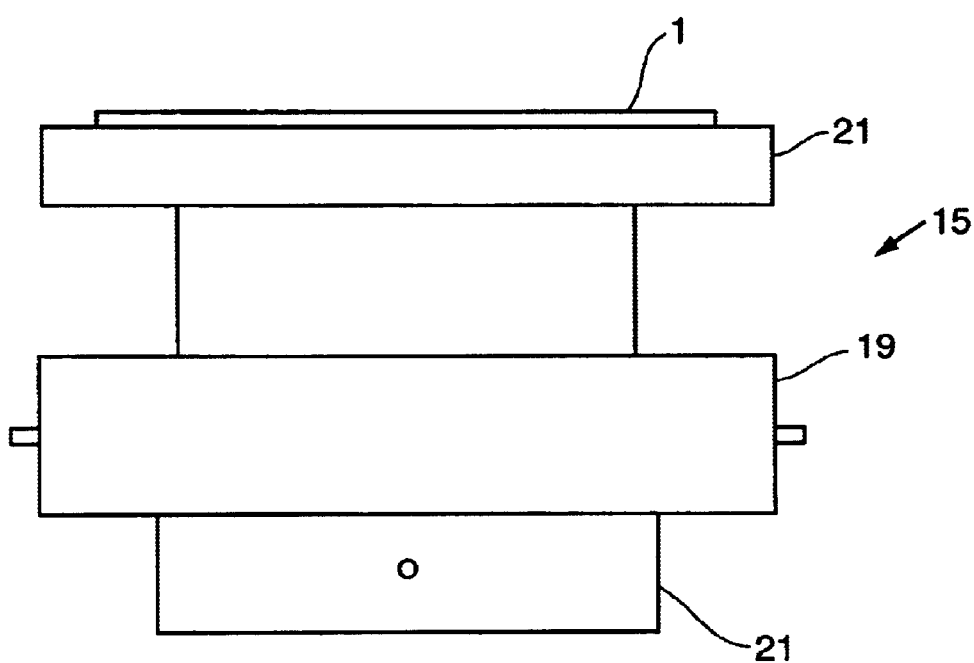
FIG. 3 shows a simplified metrology apparatus including an X, Y and theta stage for performing the inventive method.

In FIG. 3, a metrology apparatus 15 features a linear motion system including an X-stage 19 mounted on top of a Y-stage 21. The X-stage 19 carries a theta stage 17. A wafer chuck 21 is mounted on top of the theta stage to support wafer 1. The illustrated order of the stacking of the stages should not be viewed as limiting the subject invention.

Figure 1:
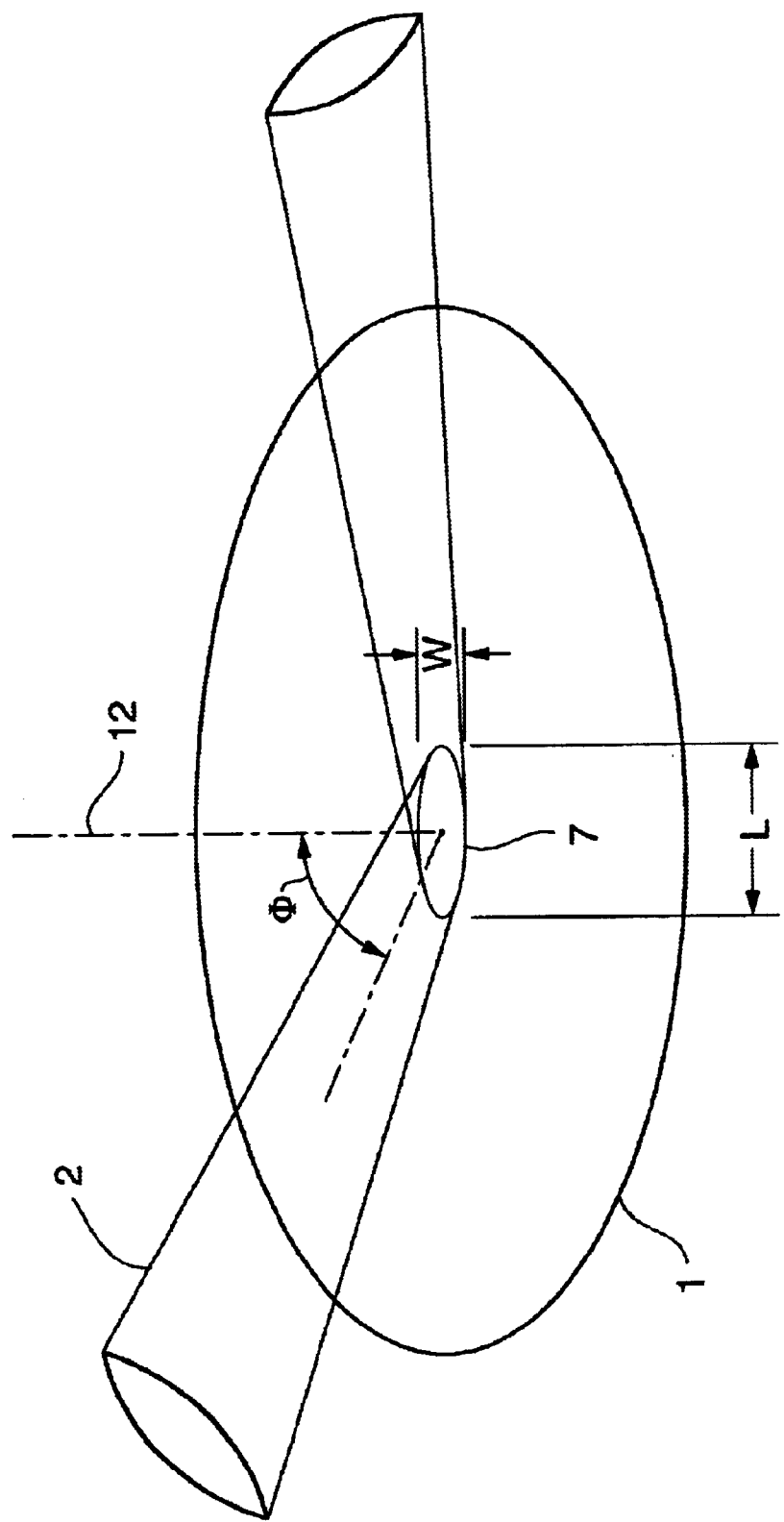
FIG. 1 shows a simplified perspective view of a probe beam incident upon the wafer at a non-normal angle of incidence.
Figure 2:
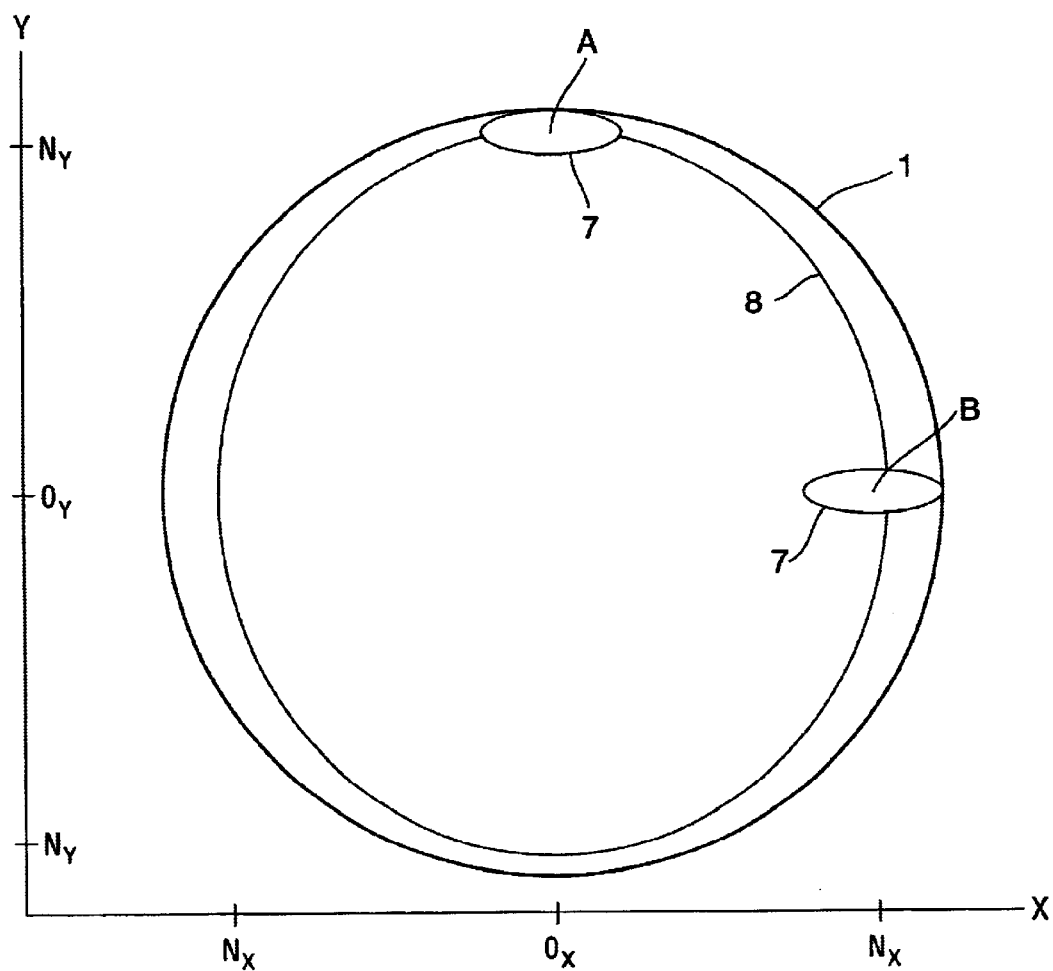
FIG. 2 shows a schematic top view illustrating the positions of an elliptical spot near the wafer's edge.
Figure 4:
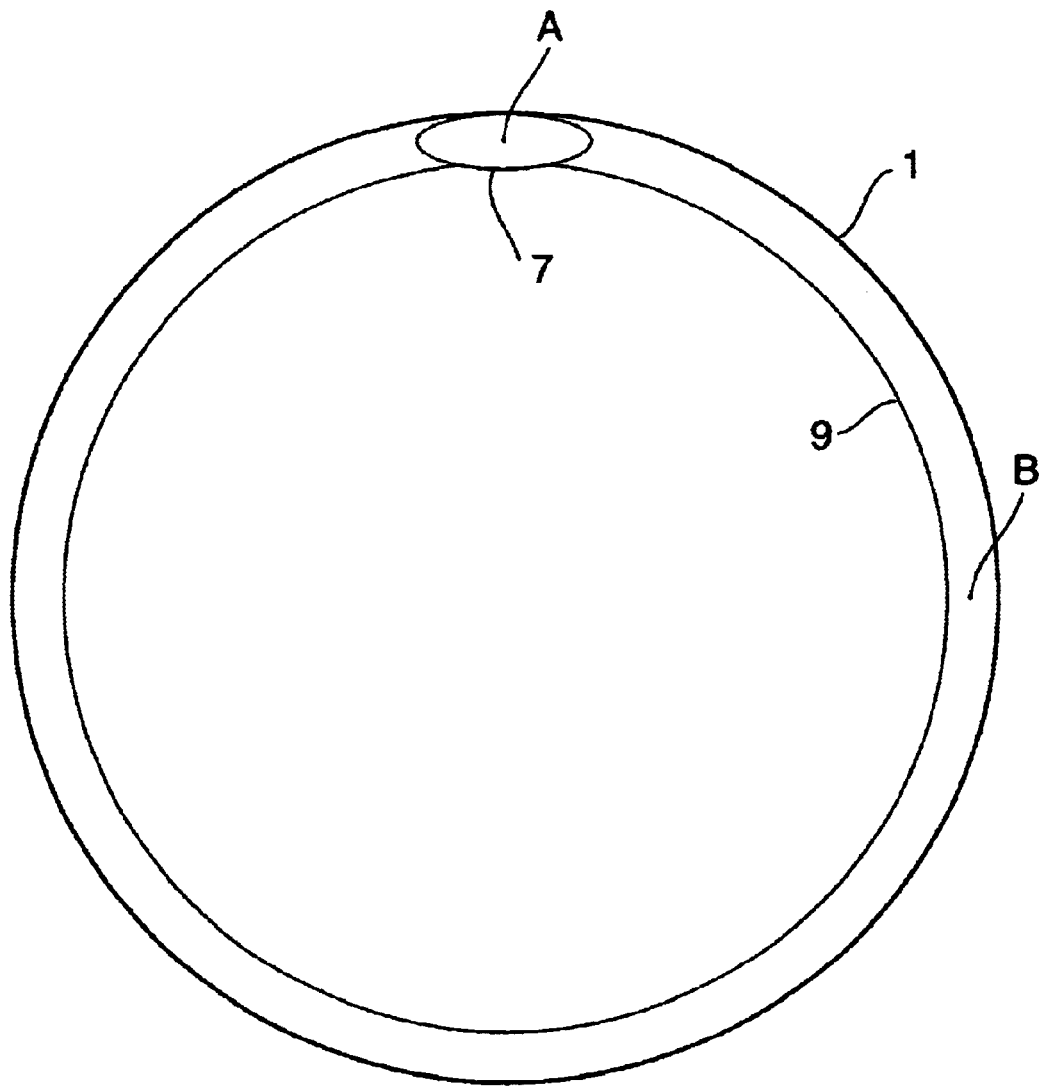
FIG. 4 shows a schematic top view of a wafer illustrating a measurement at position A.
Figure 5:
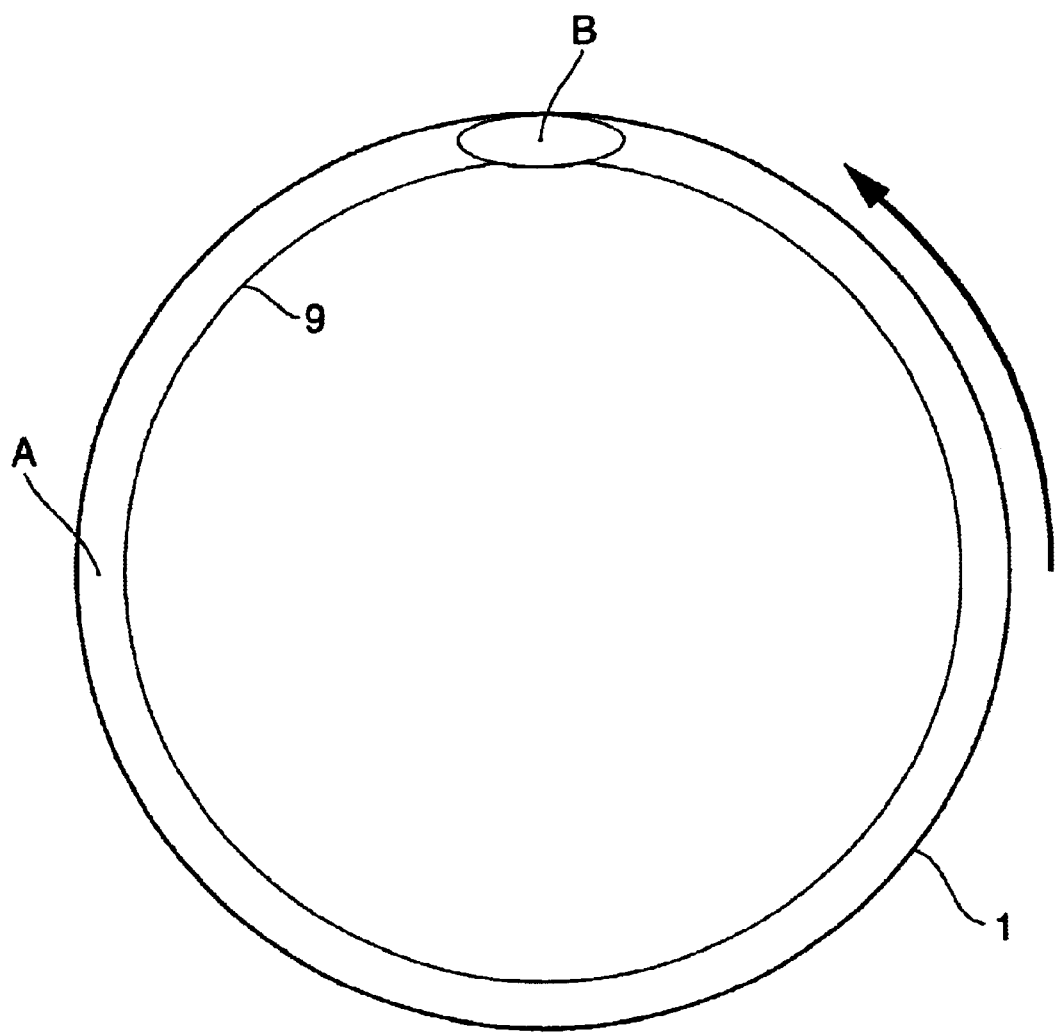
FIG. 5 shows a schematic top view of the wafer of FIG. 4 rotated 90 degrees and illustrating a measurement at position B.

In accordance with the subject invention, when it is desired to obtain a measurement in close proximity to the wafer edge, the linear stages 19, 21 move the wafer 1 in conjunction with the theta stage 17 such that the short axis W of the beam spot is substantially perpendicular to the wafer edge. As seen in FIG. 4, measurement spot A can be measured in the same manner as in the prior art. However, when point B is to be measured, the wafer is rotated 90 degrees to a position as illustrated in FIG. 5. In this orientation, elliptical spot 7 can be moved closer to the edge of the wafer as compared to the measurements shown in FIG. 2. Using the subject method, the measurement boundary is now circular in shape as illustrated by circle 9 of FIGS. 4 and 5.

For the most part, the system can be operated in a manner similar to the prior art. More specifically, the X,Y stage can be used to position the wafer with respect to the beam for any sites within the elliptical boundary 8 of FIG. 2. However, when it is desired to measure sites near the wafer edge, the theta stage can be used to rotate the wafer an amount sufficient to align the short axis of the measurement spot to be perpendicular to the edge of the wafer. In this manner, the area of exclusion can be minimized.

As is well known by those skilled in the art, various measurement protocols are designed by users. For example, one protocol might include four edge measurements and a single center measurement ($O_x$, $O_y$). Another protocol might require many more measurements over a wafer surface. It should be understood that the subject invention is broad enough to include these variations. Measurements can be taken in any order. Sites can be accessed using various combinations of X,Y and theta stage adjustments. The subject invention is invoked when it is desired to measure near an edge at a location that would have otherwise not been feasible with the prior art approach.

In a particular example, assignee herein markets an X-ray reflectometer with an X-ray probe beam directed at the sample at a high angle of incidence. The resulting elliptical spot has a short axis of about 2 to 3 mm and a long axis of between 5 and 10 mm. This spot dimension resulted in an effective edge exclusion varying from the optimum of about 1–2 mm ($O_x$, $N_y$ of FIG. 2) to the worst case of up to 10 mm ($N_x$, $O_y$ of FIG. 2). In contrast, using the method of the subject invention, the edge exclusion around the entire circumference is uniform and reduced to 1 to 2 mm.

As noted above, with respect to equation (1), the length of the long axis of the elliptical spot increases as the angle of incidence increases. Thus, the problem of edge exclusion is more severe with high angle of incidence devices such as an X-ray reflectometer.

When using the subject method, the edge exclusion is governed by the length of the short axis and is therefore independent of angle of incidence.

Although the subject method has been described in the context of using a stage with X,Y and theta movements, it may also be possible to implement the invention with other known wafer translation systems. For example, stage systems with smaller footprints such as ½X, ½Y, theta or R-theta stage combinations might be used. Also, the relative movement can be achieved with some combination of stage movement and measuring optics movement. For example, a rotary stage system can be combined with a linearly moving optics system. Alternatively, a linear stage system can be combined with a rotating optics head to obtain similar results.

What is claimed:

1. A method for inspecting a sample with a probe beam, said probe beam being focused to a spot onto the sample surface, said spot having a generally elliptical shape with a long and a short axis, with the properties of the probe beam being measured after interaction with the sample, said method for minimizing the area adjacent to the edge of the sample which cannot be accurately inspected comprising the steps of:

positioning the sample with respect to the probe beam so that the probe beam spot is adjacent the edge of the sample with the short axis being substantially perpendicular to the sample edge; and repositioning the sample with respect to the probe beam so that the probe beam spot falls on a different edge location on the sample, said repositioning step including rotating the sample with respect to the probe beam so that the probe beam spot is again positioned adjacent the edge of the sample with the short axis being substantially perpendicular to the sample edge.

2. A method of inspecting a generally circular wafer with a probe beam, said probe beam being focused to a spot onto the sample surface, said spot having a generally elliptical shape with a long and a short axis, with the properties of the probe beam being measured after reflection from the sample, said wafer being supported on a movable stage for adjusting the position of the wafer with respect to the probe beam, said stage being capable of both rotational and linear movement, said method comprising the step of:

sequentially positioning the wafer at a plurality of positions with respect to the probe beam to permit inspection of various areas on the wafer surface, and wherein when the area to be inspected is close to the edge of the wafer, rotationally positioning the wafer so that short axis of the elliptical probe beam spot is substantially perpendicular to the edge of the wafer.

* * * * *